(12) United States Patent
Wildman (10) Patent No.: US 9,298,881 B2
(45) Date of Patent: Mar. 29, 2016

(54) METHOD, SYSTEM AND DEVICE FOR VOICE MESSAGE RECORDING AND PLAYBACK AT POINT OF CARE

(75) Inventor: Timothy D. Wildman, Metamora, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 425 days.

(21) Appl. No.: 13/592,665

(22) Filed: Aug. 23, 2012

(65) Prior Publication Data

US 2014/0056417 A1 Feb. 27, 2014

(51) Int. Cl.
*H04M 1/64* (2006.01)
*G06F 19/00* (2011.01)
*H04M 3/42* (2006.01)
*H04B 1/38* (2015.01)

(52) U.S. Cl.
CPC .......... *G06F 19/327* (2013.01); *H04M 3/42221* (2013.01); *H04M 2201/40* (2013.01); *H04M 2201/60* (2013.01)

(58) Field of Classification Search
CPC .......... G08B 25/00; G08B 5/222; G08B 7/06; H04L 67/12; H04M 1/652; H04M 3/42
USPC ................... 379/88.01–88.19, 67.1
See application file for complete search history.

(56) References Cited

U.S. PATENT DOCUMENTS

| | | | |
|---|---|---|---|
| 4,539,560 A | 9/1985 | Fleck et al. | |
| 5,561,412 A | 10/1996 | Novak et al. | |
| 5,592,153 A | 1/1997 | Welling et al. | |
| 5,630,238 A | 5/1997 | Weismiller et al. | |
| 5,771,511 A | 6/1998 | Kummer et al. | |
| 5,838,223 A | 11/1998 | Gallant et al. | |
| 6,131,868 A | 10/2000 | Welling et al. | |
| 6,279,183 B1 | 8/2001 | Kummer et al. | |
| 6,481,688 B1 | 11/2002 | Welling et al. | |
| 6,486,792 B1 | 11/2002 | Moster et al. | |
| 6,560,798 B2 | 5/2003 | Welling et al. | |
| 6,761,344 B2 | 7/2004 | Welling et al. | |
| 6,781,517 B2 | 8/2004 | Moster et al. | |
| 6,958,706 B2 | 10/2005 | Chaco et al. | |
| 7,042,337 B2 * | 5/2006 | Borders et al. ........... | 340/286.07 |
| 7,069,447 B1 * | 6/2006 | Corder .................... | G06F 21/79 |
| | | | 713/168 |
| 7,092,376 B2 | 8/2006 | Schuman | |
| 7,203,287 B2 * | 4/2007 | Turner et al. ............... | 379/88.07 |
| 7,248,933 B2 | 7/2007 | Wildman | |
| 7,315,535 B2 | 1/2008 | Schuman | |
| 7,538,659 B2 | 5/2009 | Ulrich et al. | |
| 7,715,387 B2 | 5/2010 | Schuman | |
| 7,831,447 B2 | 11/2010 | Schuman | |
| 8,013,737 B2 * | 9/2011 | Tiwari et al. ............. | 340/539.22 |
| 8,046,625 B2 | 10/2011 | Ferguson et al. | |
| 8,082,160 B2 * | 12/2011 | Collins, Jr. ............ | G06F 19/327 |
| | | | 600/300 |
| 8,169,304 B2 | 5/2012 | Schuman, Sr. et al. | |
| 8,272,892 B2 | 9/2012 | McNeely et al. | |
| 2003/0052787 A1 * | 3/2003 | Zerhusen et al. .......... | 340/573.1 |
| 2003/0078071 A1 * | 4/2003 | Uchiyama ............ | H04M 1/006 |
| | | | 455/557 |

(Continued)

*Primary Examiner* — Solomon Bezuayehu
(74) *Attorney, Agent, or Firm* — Barnes & Thornburg LLP (57) ABSTRACT

A method and system for voice messaging at a point of care includes at least one point of care communication device configured to record voice messages and play back voice messages that have previously been created. The point of care communication device may be, among other things, a nurse call station or console. The recorded messages may be selectively transcribed and/or routed to other systems and/or point of care devices.

16 Claims, 5 Drawing Sheets

(56) References Cited

U.S. PATENT DOCUMENTS

| | | | |
|---|---|---|---|
| 2005/0141686 A1* | 6/2005 | Matsunaga et al. | 379/142.01 |
| 2006/0270465 A1* | 11/2006 | Lee et al. | 455/569.1 |
| 2008/0022323 A1* | 1/2008 | Koo | 725/81 |
| 2008/0068637 A1* | 3/2008 | Levy | 358/1.14 |
| 2009/0005012 A1* | 1/2009 | van Heugten | 455/413 |
| 2009/0117880 A1* | 5/2009 | Sipher | 455/412.2 |
| 2009/0212925 A1 | 8/2009 | Schuman, Sr. et al. | |
| 2009/0212956 A1 | 8/2009 | Schuman et al. | |
| 2012/0020466 A1* | 1/2012 | Dunsmuir | H04M 3/53333 379/88.04 |
| 2012/0053938 A1* | 3/2012 | Trivi | 704/235 |
| 2012/0086877 A1* | 4/2012 | Kaoh | 348/836 |
| 2012/0194327 A1* | 8/2012 | Schuman et al. | 340/286.07 |
| 2014/0047016 A1* | 2/2014 | Rao | 709/203 |
| 2014/0122244 A1* | 5/2014 | Arrasvuori et al. | 705/14.64 |

* cited by examiner

METHOD, SYSTEM AND DEVICE FOR VOICE MESSAGE RECORDING AND PLAYBACK AT POINT OF CARE

BACKGROUND

A healthcare environment, such as a hospital or other patient care facility, can include a healthcare communication system, such as a patient-nurse or "nurse call" system. These systems can enable real-time voice communication between patients and caregivers through a telecommunications infrastructure.

Some nurse call systems have a "primary station," which is configured to oversee the operation of the nurse call system for a facility and/or a specific territory within a facility, such as a nursing unit, in real time. The primary station, which is typically located in a designated staff area, may communicate with one or more secondary stations that are located throughout the monitored area. When a patient in a room of the facility places a call using the nurse call system, the primary station may receive the call. A caregiver at the primary station may respond to the call, or the system may route the call to a secondary station that may be nearer to the location of a caregiver assigned to handle the call.

SUMMARY

According to at least one aspect of this disclosure, a user station for a patient-nurse communication system includes a housing locatable in a patient care environment, the housing defining an interior region; a processor located in the interior region; and communication circuitry operably coupled to the processor. The communication circuitry receives one or more real-time voice calls at the user station and routes the real-time voice calls to one or more recipients via the patient-nurse communication system. The user station also includes a voice recorder supported by the housing; one or more speakers supported by the housing; a user interface supported by the housing, the user interface comprising at least one user-activatable control; and a memory device having embodied therein at least one processor-executable routine. The at least one route is configured to receive, at the user interface, a first request to activate the voice recorder to record a spoken message; in response to the first request, activate the voice recorder to record a message spoken by a person adjacent the user station; store the recorded message; receive, at the user interface, a second request to play the recorded message; and in response to the second request, play the recorded message at the at least one speaker.

The at least one processor-executable routine may be configured to transcribe the recorded message and store the transcribed message. The user station may include communication circuitry configured to send the transcribed message to a remote electronic medical record system. The communication circuitry may be configured according to a Health Level 7 protocol. The at least one processor-executable routine may be configured to validate the transcribed message prior to sending the transcribed message to the remote electronic medical record system. The at least one processor-executable routine may be configured to validate the first request prior to activating the voice recorder. The user interface may include a first display portion configured to display information relating to the real-time voice calls and a second display portion configured to display information relating to the recorded message. The user interface may include an indicator configured to indicate to a person that a recorded message is stored at the memory device. The at least one processor-executable routine may be configured to validate the second request prior to playing the recorded message. The user station may include a sensor to detect the presence of a person adjacent the user station, and the at least one processor-executable routine may be configured to play the recorded message in response to the detecting of the person.

According to at least one aspect of this disclosure, a point of care communication device includes a housing locatable in a patient care environment; a voice recorder supported by the housing; a user control activatable by a person to initiate a request to activate the voice recorder to record a spoken message; a processor operably coupled to the voice recorder and the user control; communication circuitry operably coupled to the processor and configured to connect the point of care device to a patient-nurse communication system; and a memory device having embodied therein at least one processor-executable routine configured to determine whether the person initiating the request to activate the voice recorder is authorized to activate the voice recorder; activate the voice recorder in response to determining that the person initiating the request is authorized to activate the voice recorder; record the spoken message; and store the recorded message for future playback at the point of care device or at another device connected to the patient-nurse communication system.

The at least one processor-executable routine may be configured to receive information identifying the person recording the spoken message and associate the recorded message with the information identifying the person recording the spoken message. The at least one processor-executable routine may be configured to receive information identifying at least one intended recipient of the recorded message other than the person recording the spoken message and associate the recorded message with the information identifying the at least one intended recipient. The at least one processor-executable routine may be configured to play the recorded message in response to a request for playback received from at least one of the intended recipients. The at least one processor-executable routine may be configured to send the recorded message to another device associated with at least one of the intended recipients. The at least one processor-executable routine may be configured to determine a message type associated with the recorded message, the message type comprising at least one of: a message intended for playback by the person who recorded the spoken message, a message intended for playback by one or more other persons, a message intended to be associated with a person's electronic medical record, a message intended to be associated with the point of care communication device, a message intended to be associated with location at which the point of care communication device is located, a message intended to be associated with a device or piece of equipment at the location at which the point of care device is located; and determining whether to allow playback of the recorded message at the point of care communication device based on the message type.

The point of care communication device may include a display configured to display a list of recorded messages available for playback at the point of care communication device, wherein the at least one processor-executable routine is configured to determine whether to include a recorded message in the list of recorded messages displayed at the point of care communication device based on at least one of the message type and information about a person requesting playback of a recorded message.

According to at least one aspect of this disclosure, a user station for a healthcare communication system includes a housing locatable in a patient care environment; a voice recorder supported by the housing; a processor operably coupled to the voice recorder; and a memory device having embodied therein at least one processor-executable routine configured to record a message spoken by a person at the voice recorder; and store the recorded message. The user station also includes communication circuitry operably coupled to the processor and configured to make the recorded message available for playback at a second user station connected to the healthcare communication system over a communication network. The at least one processor-executable routine may be configured to determine the second user station based on a location of the person who spoke the recorded message. The at least one processor-executable routine may be configured to determine the second user station based on a location of an intended recipient of the recorded message.

BRIEF DESCRIPTION OF THE DRAWINGS

This disclosure is illustrated by way of example and not by way of limitation in the accompanying figures. The figures may, alone or in combination, illustrate one or more embodiments of the disclosure. For simplicity and clarity of illustration, elements illustrated in the figures are not necessarily drawn to scale. For example, the dimensions of some elements may be exaggerated relative to other elements for clarity. Further, where considered appropriate, reference labels may be repeated among the figures to indicate corresponding or analogous elements.

DETAILED DESCRIPTION

While the concepts of the present disclosure are susceptible to various modifications and alternative forms, specific embodiments thereof are shown by way of example in the drawings and are described in detail below. It should be understood, however, that there is no intent to limit the concepts of the present disclosure to the particular forms disclosed, but on the contrary, the intention is to cover all modifications, equivalents, and alternatives consistent with the present disclosure and the appended claims.

In a healthcare environment, doctors, nurses, and other healthcare personnel are often very busy attending to a number of patients and responsibilities. These persons, as well as patients themselves, family members and other visitors, may find it easier, more natural, more effective, or more efficient to communicate information by speaking rather than using other forms of communication (such as writing on paper or entering information into a computer). Further, spoken communication carries with it nonverbal cues such as intonation, loudness, and pace, which do not ordinarily translate well to other mediums.

Figure 1:
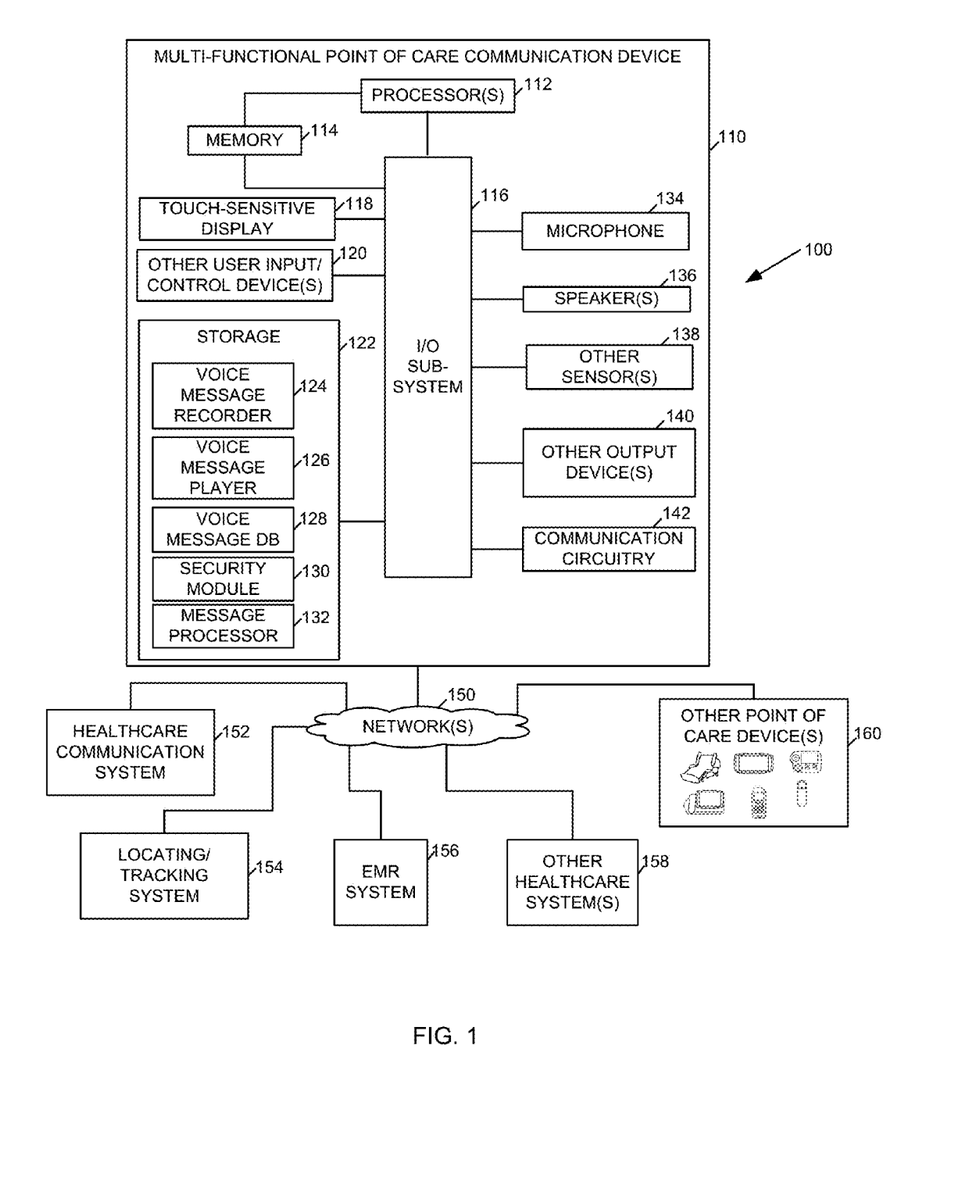
FIG. 1 is a simplified block diagram of at least one embodiment of a system for voice message recording and playback at a point of care.

Referring to FIG. 1, a system 100 enables the recording, playback, and transcription of voice messages at a point of care. Generally speaking, a 'point of care' refers to any location that is near a person that needs, may need, is receiving, or has received some form of health care, and may include patient rooms, bedside locations, patient examination rooms, emergency vehicles, rooms or centers in which diagnostic, therapeutic, clinical, surgical or other healthcare procedures are performed, observation or waiting areas, hallways or common areas within a healthcare facility, and/or others. The illustrative system 100 can route the recorded voice messages from a point of care to other devices, systems, and locations within the facility. By enabling the effective use of recorded voice communications, the system 100 can enhance the quality and/or efficiency of healthcare delivery processes.

Portions of the system 100 are embodied in a multi-functional point of care communication device ("device") 110. In the illustrative embodiments, the device 110 is a component of, or is otherwise configured to communicate with, a patient-nurse communication system or nurse call system. As such, the device 110 may be a primary station, secondary station, pillow speaker, or other device with similar functionality. Some common terms for such devices, in the nurse call context, include "master station," "audio station," "room station," "user station," "patient station," or "console," for example. This equipment generally includes at least one output device, such as a visual display or speaker, to communicate real-time calls to the user. Such stations or consoles may also include at least one input device, such as a touch screen, keypad or keyboard, microphone, telephone handset, push button, switch, dial, lever, or the like, to enable the user to place and/or respond to the real-time calls.

The illustrative device 110 is typically located at or near a point of care. For example, the device 110 may be embodied as a user station mounted to a wall, headwall, column, bed, siderail or other structure in a patient's room, an electronic status board mounted in a hallway or common area of a healthcare facility, or a pillow speaker tethered to a bed located in a room of the facility. In some embodiments, aspects of the device 110 may be embodied in a general-purpose computing device, such as a server, desktop computer, or mobile computing device (e.g., a computing device that is handheld or otherwise portable, such as a smartphone, laptop, tablet computer, etc.).

As shown in FIG. 1, the device 110 includes one or more processors 112 (e.g. microprocessor, microcontroller, digital signal processor, etc.), computer memory 114, and an input/output (I/O) subsystem 116. Although not specifically shown, it should be understood that the I/O subsystem 116 typically includes, among other things, an I/O controller, a memory controller, and one or more I/O ports, to enable communication between the processor 112, the memory 114 and the various components 118, 120, 122, 134, 136, 138, 140, 142 connected thereto. The memory 114 may be embodied as any type of suitable computer memory device (e.g., volatile memory such as various forms of random access memory). The I/O subsystem 116 is communicatively coupled to at least one touch-sensitive display 118 (e.g., a touch screen, touch-sensitive interactive controls, virtual keypad, etc.), one or more other input or user control devices 120 (e.g., a physical keyboard or keypad, buttons, levers, dials, etc.), at least one data storage device 122, a microphone 134, one or more speakers 136, one or more sensors 138 (e.g., a proximity sensor or wireless locating and tracking sensor such as an infrared or radio-frequency (RFID) tracking device), other output devices 140 (e.g., an LED indicator, display screen, etc.), and communication circuitry 142.

The data storage 122 may include one or more hard drives or other suitable data storage devices (e.g., flash memory, memory cards, memory sticks, and/or others). In the illustrative embodiment, all or portions of a voice message recorder 124, a voice message player 126, a voice message database 128, a security module 130, and a message processor 132 reside at least temporarily in the data storage 122. Portions of the voice message recorder 124, the voice message player 126, the voice message database 128, the security module 130, and/or the message processor 132 may be copied to the memory 114 during operation, for faster processing or other reasons. Further, in some embodiments, portions of any of the voice message recorder 124, the voice message player 126, the voice message database 128, the security module 130, and/or the message processor 132 may be specially configured for use in connection with a particular hardware platform or configuration, such as a particular implementation of a healthcare communication system, computing device or operating system. In some embodiments, the voice message recorder 124, the voice message player 126, the voice message database 128, the security module 130, and/or the message processor 132 may include a local portion (which may include a client application or front-end user interface and a back end or server application) and one or more remote or distributed portions (which may similarly include portions of the client application or front-end user interface and back end or server application). For example, in some embodiments, recorded voice messages may be stored on a computer server with which the device 110 communicates via a network 150 (e.g., at a local or remote data center).

Each of the voice message recorder 124, voice message player 126, voice message database 128, security module 130, and message processor 132 is embodied as computer software, firmware, hardware, data structures (e.g., files, tables, databases, etc.) or a combination thereof. The voice message recorder 124 processes a voice message received live by the microphone 134 and converts it into a digital form that can be stored in computer memory (at the device 110 or another storage location) and otherwise processed and used as described herein. The voice message player 126 accesses the previously recorded and stored voice messages from memory and plays them through the speaker 136 upon the request of a user of the device 110 or some other triggering event (such as the detection by the locating and tracking system 154 of a person entering the room in which the device 110 is located, for example).

The voice message database 128 stores the recorded voice messages in computer memory, along with any associated information, so that the recorded voice messages can be retrieved and played at a later time. Some examples of information that may be associated with voice messages in the database 128 include identifying information relating to the person that created the voice message, identifying information relating to a subject or topic of the voice message (e.g., a patient, device, or topic identifier), the date and time the message was created, and a message type (described below). Generally speaking, the database 128 is configured for keyword and/or meta data searching by the system 100, so that information pertaining to voice messages can be retrieved and displayed at the touch-sensitive display 118 and/or other output devices 140, or at another system 152, 154, 156, 158 or device 160.

The security module 130 authenticates users who wish to record voice messages or desire access to recorded voice messages stored by the system 100. The security module 130 operates a user interface by which systems personnel and/or others can configure rules for determining whether particular persons are permitted to create, play, transcribe, or send recorded messages via the system 100, and applies those rules when the system 100 is in use. The message processor 132 processes voice messages in accordance with the requirements of a particular design or implementation of the system 100. For example, in some embodiments, the message processor 132 invokes voice to text transcription routines to transcribe recorded messages and store them in text form. In some embodiments, the message processor 132 configures the stored voice messages for transmission to other systems or devices in conformance with various communication protocols as may be needed (e.g., a Health Level 7 or HL7 protocol).

The communication circuitry 140 communicatively couples the device 110 to one or more other devices and/or systems 152, 154, 156, 158, 160 via one or more networks 150. The network(s) 150 may include a local area network, wide area network, secure enterprise cloud, secure portions of the Internet, and/or others. Accordingly, the communication circuitry 140 may include wired and/or wireless Ethernet, mobile/cell network, WI-FI, BLUETOOTH, virtual private network (VPN), or near-field communication (NFC) circuitry or other suitable interface mechanisms as may be needed, pursuant to the specifications and/or design of the particular network(s) 150.

In some embodiments, intermediate devices and/or circuitry enable the device 110 to interface with one or more of the devices and/or systems 152, 154, 156, 158, 160. For example, an input-output (I/O) board and a switch (e.g., a Power over Ethernet (POE) switch) may be used to communicatively couple the device 110 to the healthcare communication system 152 (e.g., a nurse call system). These additional devices and/or circuitry often convert device-specific protocols from a variety of devices, which may be installed in patient rooms, to a network protocol suitable for communication over a network. For example, I/O boards may convert serial communications to XML-over-TCP/IP. To enable the transmission of voice communications over the network(s) 150, portions of the system 100 (e.g., one or more intermediate servers) may be equipped with soft telephony switches and related componentry.

The device 110 may include other components not illustrated in FIG. 1 for clarity of the description. In general, the components of the device 110 and the system 100 are communicatively coupled as shown in FIG. 1 by one or more signal paths. Such signal paths may be embodied as any type of wired or wireless signal paths capable of facilitating communication between the respective components of the device 110 and the system 100. Portions of the system 100 may be embodied as one or more stand-alone software applications or may be incorporated into or accessed by one or more other software applications. For example, portions of the system 100 may be incorporated into other systems or interactive software applications.

Some examples of systems and/or devices with which the device 110 may communicate via the network(s) 150 include the healthcare communication system 152, a locating and tracking system 154, an electronic medial records (EMR) system 156, other healthcare systems(s) 158 (which may include, for example, an admission, discharge, and transfer (ADT) system, and/or others), and other point of care devices 160 (such as hospital beds and other hospital equipment and other multi-functional communication devices).

As mentioned above, the healthcare communication system 152 may include a nurse call system. Some embodiments of the system 152 include one or more primary user consoles or stations and one or more secondary user consoles or stations that are configured to be operated by nurses or other healthcare facility staff. In general, primary and secondary stations enable nurses or other staff to place real-time voice calls, cancel calls, monitor the location of other staff members, process calls and alerts and route or relay calls or alerts to and from other consoles or other components of the system. Generally speaking, the term "call"' is used herein to refer to voice calls that are made in real-time via, e.g., a nurse call system (e.g., a "live" connection as opposed to a communication that is recorded for later listening). One or more of the primary and/or secondary stations may include features of the device 110 in some embodiments of the system 100.

In the healthcare communication system 152, one or more server computers may be configured to operate and manage the nurse call functions, such as receiving and managing communications from various connected devices, synchronizing devices that come online, controlling placement and canceling of calls, answering of calls, generating of notifications or alerts, acknowledging and canceling of notifications and alerts, managing location information for staff and devices, managing staff-patient assignments, assigning and managing roles and responsibilities to staff and devices, and managing patient information and patient discharges and transfers.

The healthcare communication system 152 may include one or more additional servers or other devices to interface with other systems or services. For example, the healthcare communication system 152 may be coupled to a telecommunications server, which acts as a gateway to a healthcare facility's telecommunications infrastructure. Such an infrastructure generally includes a network that facilitates communication among a variety of telecommunication devices, including analog and digital devices, fixed telephones and mobile or cellular devices, personal data assistants (PDAs), pagers and the like. For example, a facility's telecommunications infrastructure may include a public switched telephone network (PSTN), private branch exchange (PBX), or the like.

Some embodiments of the healthcare communication system 152 may include a Voice Over Internet Protocol (VOIP) server configured to translate system operations and communications to corresponding messages that are then delivered to endpoint devices, such as nurse or staff stations, consoles or room input/output boards. Such a server may provide integration with the hospital telecommunications structure (e.g., PBX or other voice communication system).

In some embodiments, other services and systems may be in communication with the healthcare communication system 152 to support its features and functionality. Such other services or systems may include a database server, one or more wireless communications servers for managing communications to and from wireless telecommunications devices and/or wireless badges for locating and tracking of staff members, a user authentication server for managing user accounts, passwords, and user authorizations; a hospital administrative client for conducting administrative tasks relating to patients and staff, such as adding patients and assigning staff to patients; and a status or reports server for managing the display and reporting of calls for one or more locations in the facility.

Some other examples of servers that may be used in connection with the healthcare communication system 152 include a server to provide communication and configuration for wireless devices (using, e.g., EMERGIN WIRELESS OFFICE); a server to provide communication and configuration for, e.g., wireless VOCERA devices; a server to interface with an alerting system (e.g., HILL-ROM NAVICARE) to receive and process alerts therefrom; and a server to operate an electronic status board. As used herein, the term "server" is meant to refer to any device capable of performing the described functionality and any associated software programs or services relating thereto, which may be resident on and/or executable by any computer, device or equipment in the system or more than one computer, device or equipment in the network.

In some embodiments, the device 110 interfaces with a healthcare facility's person and/or asset locating and tracking system 154. The system 154 may include wireless (i.e. infrared or radio frequency) location tracking receivers or "remote location receivers" and related location tracking badges or tags. These devices may be coupled to the network(s) 150 via I/O boards or through nurse call system consoles or stations using, e.g., RS485 connections.

In some embodiments, the device 110 sends recorded messages or transcribed versions thereof to the EMR system 156 and/or other healthcare system(s) 158. For example, a voice message recorded at the device 110 may be linked with a patient's medical history and stored in the EMR system 156. As another example, a voice message recorded at the device 110 may be linked with a patient's transfer history or discharge information in an ADT system 158.

Some examples of other point of care devices 160 with which the device 110 may communicate include hospital beds, chairs, stretchers, patient lift mechanisms and the like, which may be linked to the system 100 via bed interface units, audio bed station connectors (ASBCs), 37-pin connectors, or other connector devices; as well as patient monitors and other medical or clinical devices or equipment (such as therapy equipment, heart rate or respiration monitoring devices, and the like). Other devices 160 may also include mobile communication devices carried by caregivers or staff members, such as cellular phones, smartphones, personal digital assistances, tablet computers, VOCERA devices, and the like. One or more of such devices may include features of the device 110 in some embodiments of the system 100.

Figure 2:
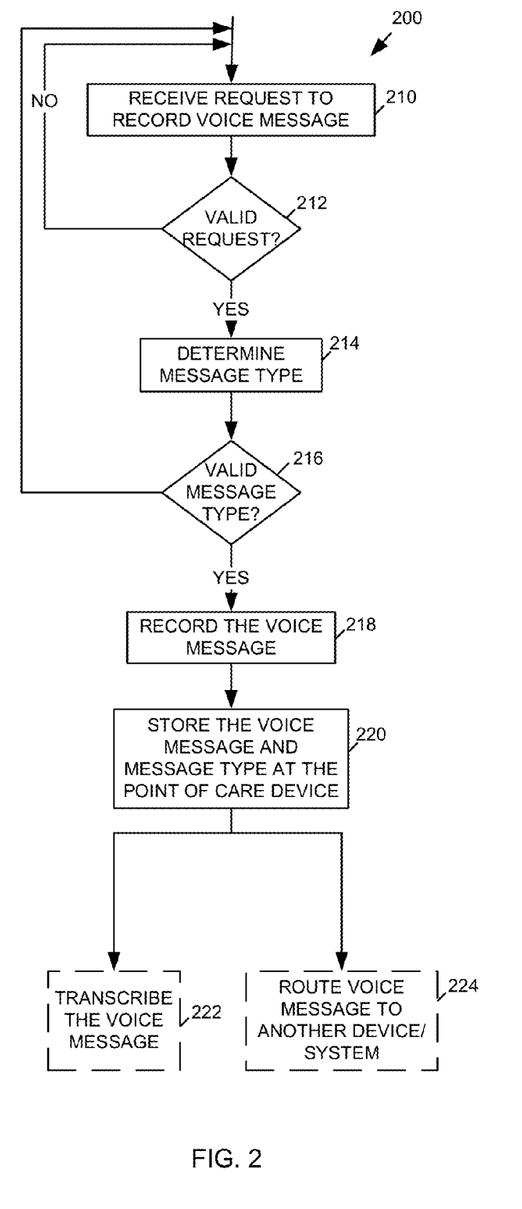
FIG. 2 is a simplified flow diagram of at least one embodiment of a method for recording a voice message at a point of care.

Referring now to FIG. 2, an illustrative method 200 executable as computerized programs, routines, logic and/or instructions by the device 110 and/or one or more of the other aspects of the system 100 to record voice messages at a point of care is shown. At block 210, the method 200 receives a request to record a voice message. Such a request may be initiated by a person at the device 110 using any suitable form. For example, the person may contact a "record a voice message" user control on the touch-sensitive display 118 to initiate the method 200.

At block 212, the method 200 determines whether the person desiring to record a voice message at the device 110 is authorized to do so. This can be done in any number of different ways, including by requiring the person to input a personal identification number (PIN) or other identifier and/or password. Alternatively or in addition, the method 200 may authenticate the person using a wireless technique using, e.g., an RFID or infrared reader or bar code scanner, which may be integrated with the device 110 as mentioned above. Such a reader or scanner may be configured to read user identification information actively or passively transmitted by an ID badge or tag worn or carried by the user. The method 200 proceeds to block 214 if it successfully validates the person making the request to record a voice message, and returns to block 210 (e.g., to await another request) if the validation attempt is unsuccessful. A request to record a voice message at the device 110 may be denied if, for example, the caregiver making the request has not been assigned to a patient or room that is associated with the point of care, if the person making the request is not employed by the healthcare facility, or for myriad other reasons. Rules for determining whether various potential requesters are permitted to record voice messages at the device 110 can be defined or pre-configured by, e.g., a system administrator for the healthcare facility, and implemented in the system 100 using computerized programs, routines, logic and/or instructions (via, e.g., the security module 130).

At block 214, the method 200 determines the type of message desired to be recorded by the requesting person. In some embodiments, the method 200 presents the user with a number of choices of possible message types (which may be defined or configured by, e.g., a system administrator for the healthcare facility), and allows the user to select one of the choices. Some examples of possible message types include public and private messages, messages associated with a particular patient, location (e.g., patient room) or device (e.g., a bed within a patient room), and messages that are associated with certain groups of people (e.g., caregivers, housekeeping personnel, service technicians, patient's family members, visitors, etc.). For instance, certain messages may be intended for playback only by the person who recorded the spoken message, while other messages may be intended for playback by a certain person other than the person who recorded the message. Further, some messages may be intended for playback by a selected group of persons (e.g., caregivers responsible for a particular patient, floor, or wing of a healthcare facility, housekeeping staff, service technicians, etc.), and still other messages may be intended for playback by the general public. Alternatively or in addition, some messages may be specific to a particular patient and/or intended to be associated with a person's electronic medical record or ADT record, while other messages may be intended to be associated with the device 110, a location of the device 110, or something else at the point of care location (e.g., a bed or other piece of equipment). Once the user selects or otherwise inputs the desired message type, the method 200 proceeds to block 216.

At block 216, the method determines whether the person desiring to record a voice message at the device 110 is permitted to record messages of the selected type. The method 200 proceeds to block 218 if it successfully validates the message type for the requester, and returns to block 210 (e.g., to await another request) or block 214 (e.g., to await another message type selection) if the validation attempt is unsuccessful. A request to record a voice message of a certain type may be denied if, for example, the requester has selected a message type that conflicts with the requester's own assigned role or group. As an example, permission may be denied to a service technician if the technician attempts to select a message type that is associated with a particular patient, or for any number of other reasons. Rules for determining whether various potential requesters are permitted to record voice messages of certain types can be defined or pre-configured by, e.g., a system administrator for the healthcare facility, and implemented in the system 100 using computerized programs, routines, logic and/or instructions (via, e.g., the security module 130).

At block 218, the method 200 activates the microphone 134 and the voice message recorder 124 to record a spoken message at the point of care. The method discontinues recording in response to user input (e.g., pressing a 'stop' button or saying the word 'end'), or automatically (e.g., after the elapse of an amount of time in which no spoken words are detected). The recorded voice message, as well as its associated message type, requester information, and other associated information are stored in computer memory at the device 110 and/or another location (e.g., a local or remote server or data center), at block 220.

If the requesting person is authorized to record a message of the selected type, then depending on the message type, the method 200 may prompt the user for additional information either before or after the message is recorded (e.g., at block 216, 218, or 220). For example, if the message pertains to a particular patient, the method 200 may prompt the user to enter information identifying the patient, so that the voice message can be linked with the patient's records (e.g., EMR or ADT record). If the message pertains to a particular location or device, or is to be shared with all of the members of a selected group, the method may prompt the user to input the appropriate details so that the message can be appropriately linked with the location, device, or group. In some embodiments, the method 200 may determine the necessary links automatically through the use of inputs from the locating and tracking system 154 and/or other systems. For example, the method 200 may obtain information about the user's identity and/or location from the locating and tracking system 154 (e.g., via the user's ID tag) and associate that information with the recorded voice message (using, e.g., the voice message database 128).

Once a voice message and its associated information have been recorded and saved at the device 110, there are many possible things that the system 100 may do with the message. In some embodiments, the method 200 transcribes the voice message to text form and stores the transcribed message in computer memory, at block 222. In some embodiments, transcription capabilities are performed by the method 200 invoking any one of the several voice to text transcription software applications that are commercially available, which may be stored at and executed by the device 110 or at another device (e.g., a server). In some embodiments, the method 200 sends the original and/or transcribed voice message and related information, as appropriate, to one or more other devices and/or systems, at block 224. For instance, the method 200 may send the recorded voice message and associated caregiver identifier to the healthcare communication system 152, which then routes the voice message to the caregiver at a location detected by the locating and tracking system 154. As another example, the method 200 may send the transcribed message and associated patient identifier to the EMR system 156, which then attaches the transcribed message to the patient's medical record.

Figure 3:
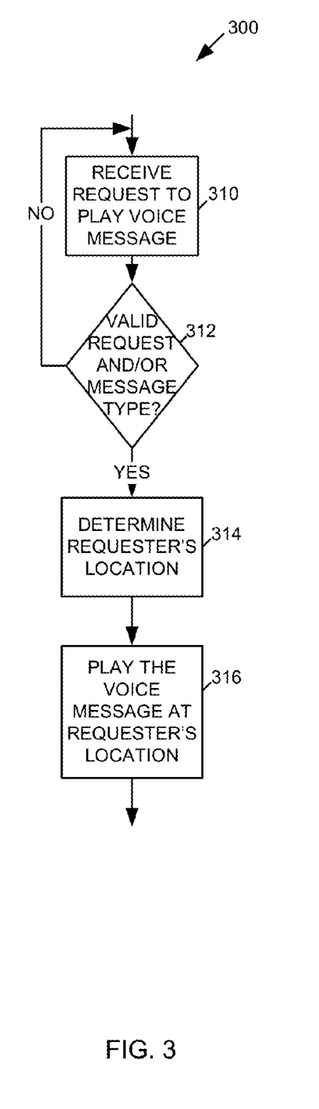
FIG. 3 is a simplified flow diagram of at least one embodiment of a method for playing a recorded voice message at a point of care.

Referring now to FIG. 3, an illustrative method 300 executable as computerized programs, routines, logic and/or instructions by the device 110 and/or one or more of the other aspects of the system 100 to play previously-recorded voice messages at a point of care is shown. At block 310, the method 300 receives a request at the device 110 to play a previously-recorded voice message. Such a request may be initiated by a person at the device 110 using any suitable form. For example, the person may select a message from a list of voice messages displayed on the touch-sensitive display and then contact a "play voice message" user control on the touch-sensitive display 118. In some embodiments, such "requests" are generated automatically by the system 100. For example, in some embodiments, the method 300 may detect a person entering a particular patient's room via the locating and tracking system 154, determine (based on, e.g., signals transmitted by the person's ID tag) that the person entering the room has permission to listen to certain voice messages, and automatically begin playing those messages while the person is in the room. In either case, the illustrative method 300 proceeds to blocks 312 and 314 before playing the requested message. In other embodiments, the method 300 may proceed directly from block 310 or 312 to block 316.

At block 312, the method 300 validates the request to play a voice message and/or the message type. That is, the method 300 determines whether the person desiring to play a voice message at the device 110 is authorized to do so, and also verifies that such person is permitted to listen to voice messages of the type corresponding to the selected message. This can be done in any number of different ways, such as any of those described above with reference to blocks 212 and 216 of FIG. 2. As an example, some persons may not be permitted to listen to voice messages that contain sensitive patient information, but may be permitted to listen to voice messages that pertain to the status of the patient's room, hospital bed or other equipment. The method 300 proceeds to block 314 if the requester is permitted to listen to prerecorded voice messages of the selected type, and returns to block 310 (e.g., to await a request from another requester or a different request from the same requester), if the validation is not successful.

In some embodiments, at block 314, the method 300 determines the location of the person requesting playback of a stored voice message at the device 110. This may be done via the locating and tracking system 154 as described above. The method 300 may use the location information to route messages recorded at other devices to the requester at his or her current location. For example, a caregiver may record a voice message, such as a personal reminder or "note to self," at a device 110 (e.g., a nurse call station or console) while in one patient room, but desire access to that message later when he or she is attending to a patient in another room or elsewhere in the facility.

As another example, a caregiver may record a message intended for one or a number of other people using the device 110 at one location. For instance, a caregiver may leave a voice message at the device 110 for the next caregiver assigned to the area in which the device 110 is located (e.g., on the next shift); thereby eliminating the need for potentially time consuming or disruptive shift change meetings. The recipient(s) may then access and listen to the message at the same device 110 once they arrive there, or from wherever they are in the facility (e.g., at other nurse call stations or consoles). Aspects of the nurse call system and/or the healthcare facility's telecommunications infrastructure facilitate the routing of recorded messages to other locations. Once the requesting person's identity has been validated and his or her permitted access level checked, and his or her current location determined, the method 300 plays the selected voice message through the speaker 134, at block 316.

Figure 4:
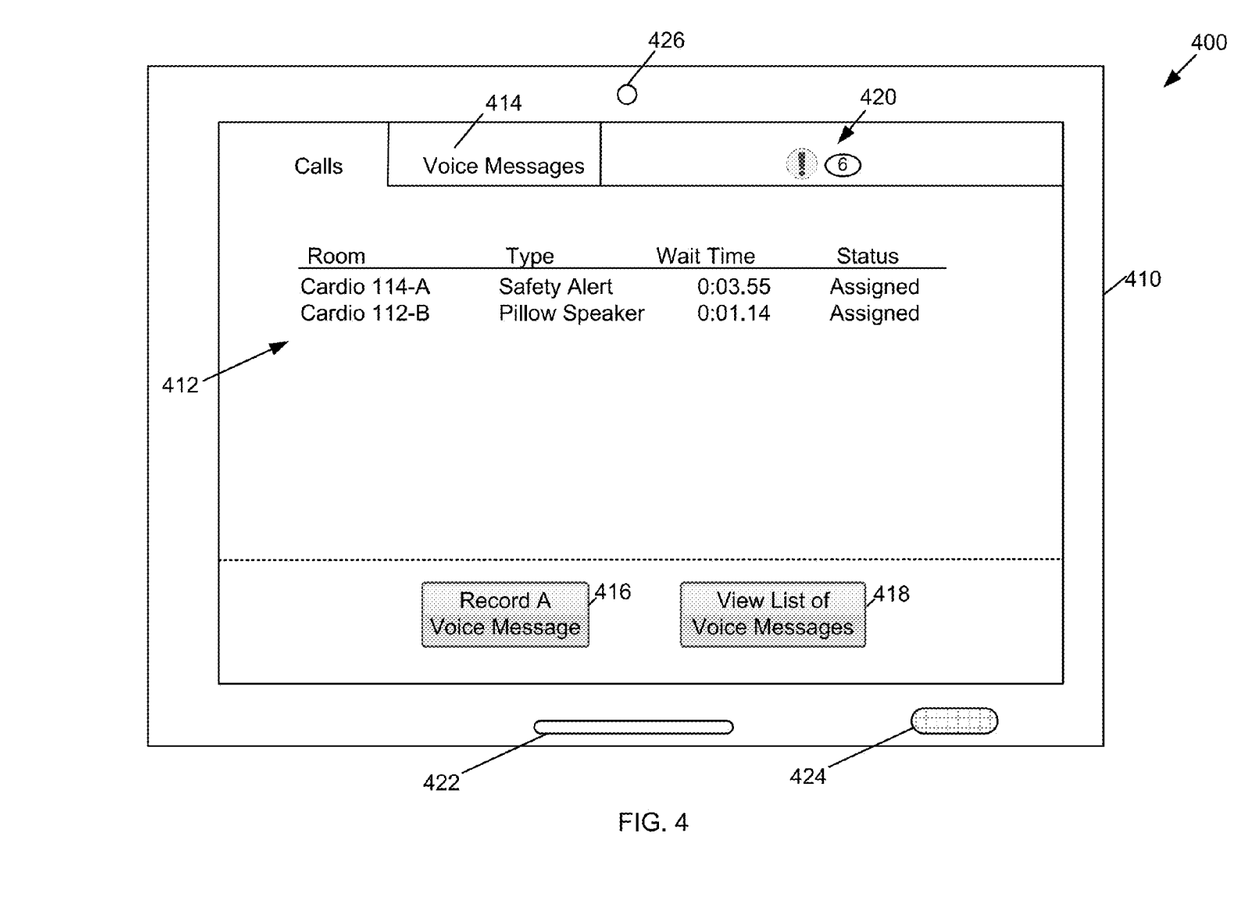
FIG. 4 is a simplified front elevational view of at least one embodiment of a multi-functional point of care communication device including an exemplary user interface.

Referring now to FIG. 4, an embodiment 400 of the device 110 is shown. The illustrative embodiment 400 is a user station or console for a nurse call system. The embodiment 400 includes a housing 410, which supports a touch screen user interface 412, a microphone 422, a speaker 424, and a locating/tracking sensor 426. The user interface 412 includes a "calls" portion, in which a list of pending real-time calls is displayed, and a "voice messages" portion 414 in which a list of recorded voice messages stored at the device 110 may be displayed if the user is validated as described above. The user interface 412 includes interactive controls such as a "record a voice message" button 416 and a "view list of voice messages" button 418. The user interface 412 also includes dynamic informational icons such as an icon 420. The icon 420 is displayed to let the user know that there are recorded messages stored at the device. The icon 420 includes an indicator (e.g., a number inside a circle) indicating the number of recorded messages that are available to be listed to or have not yet been listened to.

Figure 5:
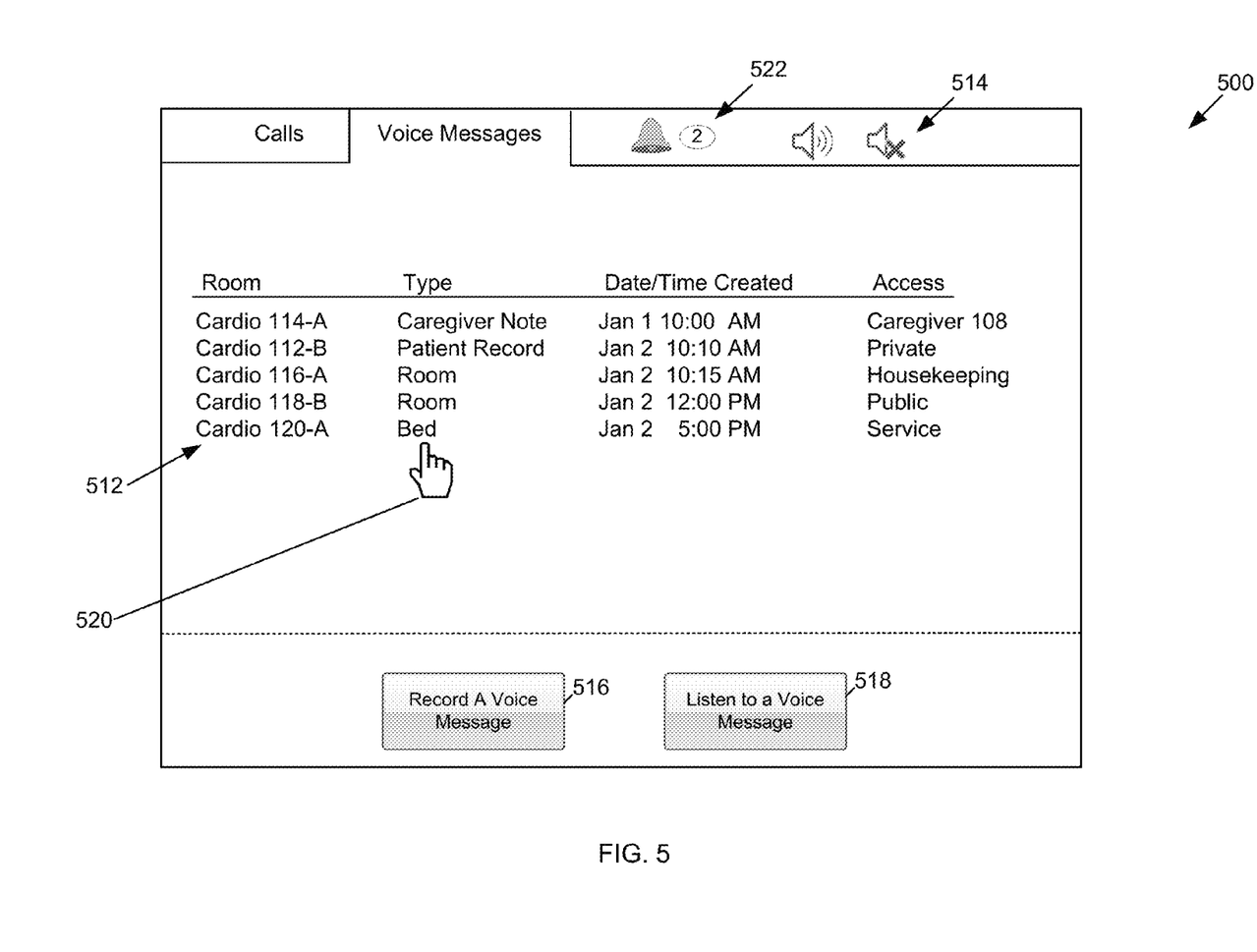
FIG. 5 is a simplified elevational view of at least one embodiment of another user interface for a multi-functional point of care communication device.

In the housing 410 (portions of which may be manufactured using, e.g., plastic and/or other materials), the illustrative station 400 includes IEEE 802.3-compliant components so that it can be powered by Power over Ethernet (PoE) network switches. The circuitry of the station 400 also includes componentry that incorporates session initiation protocol (SIP) voice over Internet protocol (VoIP) within the station itself. Regarding the user interface 412, enhanced graphics capabilities may be used, for example to selectively highlight or shade certain areas of the display of either the listing of calls or the listing of recorded voice messages (FIG. 5). In some embodiments, the user interface 412 may be implemented using a Super Video Graphics Array (SVGA) touch display, or a VGA (or higher) resolution touch display.

Referring now to FIG. 5, an illustrative user interface 500 for the device 110 (e.g., the user station of FIG. 400), which displays a listing of recorded voice messages 512, is shown. Items in the listing 512 may be individually selected for playback or a display of message details, through the touch-sensitive display as shown by the selector graphic 520. The listing 512 identifies the location at which the voice message was recorded, the message type, the date and time created, and the security access level. Other information about the recorded voice messages may be displayed, alternatively or in addition, in accordance with the requirements of a particular design or implementation of the system 100.

The user interface 500 includes interactive controls 516, 518, which can be activated by a user to record a voice message or listen to a previously-recorded voice message, respectively. The user interface 500 also includes dynamic informational icons such as an icon 522. The icon 522 is similar to the icon 420, discussed above, except that it relates to real-time calls rather than recorded voice messages. In some embodiments, the icon 522 may be displayed only when the "calls" screen is not active, and the icon 420 may be displayed only when the "voice messages" screen is not active. The user interface 500 also includes interactive controls 514, which allow the user to adjust or turn off the sound volume when the user is listening to a recorded message.

Figure 6:
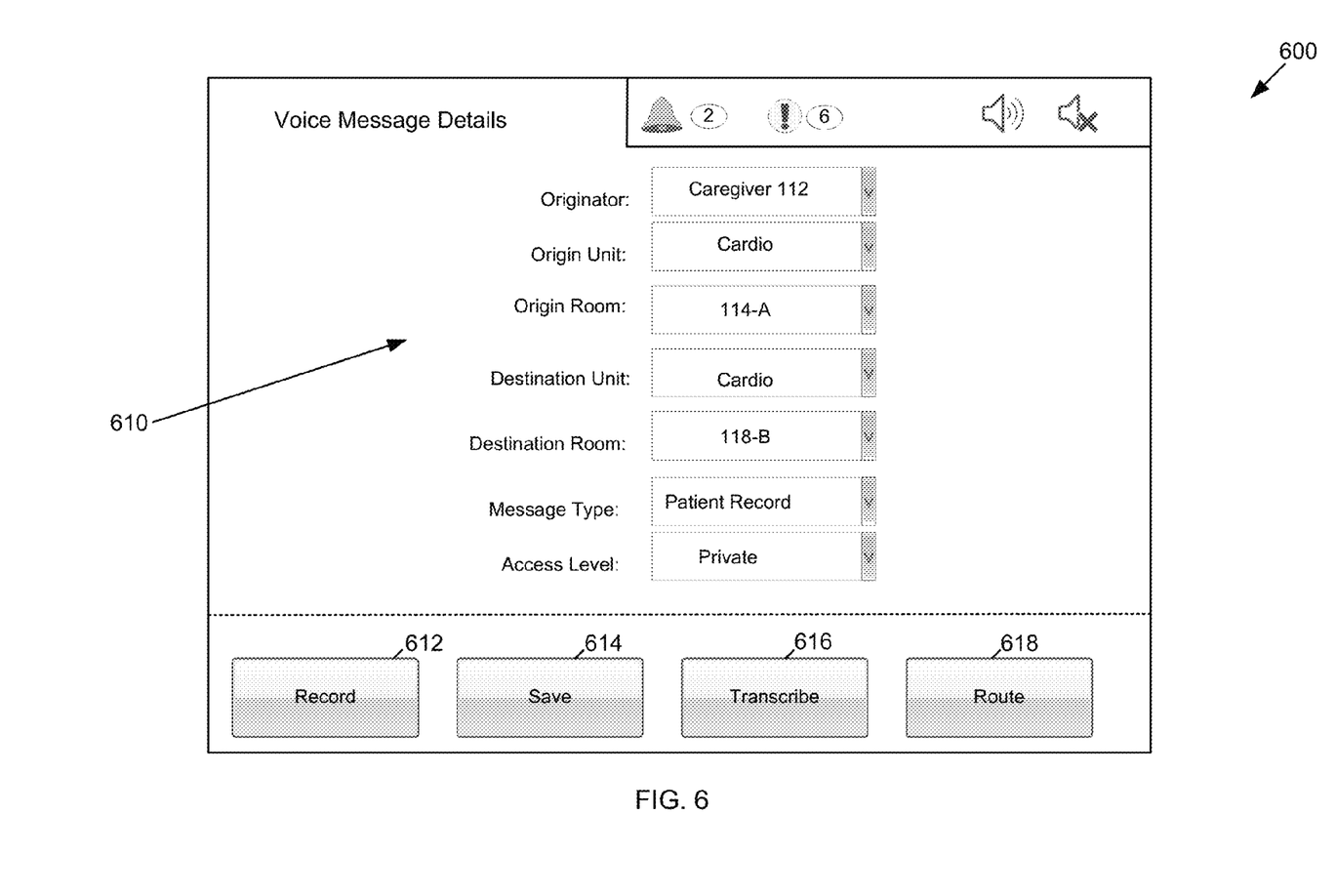
FIG. 6 is a simplified elevational view of at least one embodiment of another user interface for a multi-functional point of care communication device.

Referring now to FIG. 6, an illustrative user interface 600 for the device 110 (e.g., the user station of FIG. 400), which permits the person creating a voice message to input informational details relating to the recorded message. As such, the user interface 600 includes an interactive fill-in form 610, in which information such as the originator (the person who recorded the message), the originator's location (e.g., unit and/or room), message destination (e.g., the unit and/or room to which the recorded message is to be routed), the message type, and the access level associated with the recorded message. The interactive controls 612, 514, 616, 618 enable the user to record the voice message, save the recorded message to computer memory, transcribe the recorded message, or route the recorded message to another location, device or system, respectively, as discussed above.

The foregoing disclosure is to be considered as exemplary and not restrictive in character, and all variations and modifications that come within the spirit of the disclosure are desired to be protected. Further, while aspects of the present disclosure may be described in the context of particular devices and systems, it should be understood that the various aspects have other applications, for example, in other systems in which voice message capabilities may be desired.

The invention claimed is:

1. A user station for a patient-nurse communication system, the user station comprising:
   a housing locatable in a patient care environment, the housing defining an interior region;
   a processor located in the interior region;
   communication circuitry operably coupled to the processor, the communication circuitry configured to receive one or more real-time voice calls at the user station and route the real-time voice calls to one or more recipients via the patient-nurse communication system;
   a voice recorder supported by the housing;
   at least one speaker supported by the housing;
   a user interface supported by the housing, the user interface comprising at least one user-activatable control; and
   a memory device having embodied therein at least one processor-executable routine configured to:
      receive, at the user interface, a first request from a first person to activate the voice recorder to record a spoken message;
      authenticate the first request by determining that the first person has authority to make a recording at the user station based on an identity of the first person as determined from a first wireless signal emitted by a first tag worn by the first person;
      in response to authenticating the first request, activate the voice recorder to record a message spoken by a person adjacent the user station;
      store the recorded message;
      receive, at the user interface, an input from the first person indicating at least one second person who is authorized to listen to the recorded message;
      receive, at the user interface, a second request from the at least one second person to play the recorded message;
      authenticate the second request by determining that the second person has authority to play the recording at the user station based on an identity of the second person as determined from a second wireless signal emitted by a second tag worn by the second person;
      in response to authenticating the second request, play the recorded message through the at least one speaker, wherein persons not authorized to use the user station for recording or playing messages are unable to do so;
      transcribe the recorded message and store the transcribed message;
      validate the transcribed message prior to sending the transcribed message to a remote electronic medical record system; and
      send the transcribed message to the remote electronic medical record system.

2. The user station of claim 1, wherein the communication circuitry is configured according to a Health Level 7 protocol.

3. The user station of claim 1, wherein the user interface comprises a first display portion configured to display information relating to the real-time voice calls and a second display portion configured to display information relating to the recorded message.

4. The user station of claim 1, wherein the user interface comprises an indicator configured to indicate to a person that a recorded message is stored at the memory device.

5. The user station of claim 1, comprising a sensor to detect the presence of a person adjacent the user station, wherein the at least one processor-executable routine is configured to play the recorded message in response to the detecting of the person.

6. A point of care communication device comprising:
   a housing locatable in a patient care environment;
   a voice recorder supported by the housing;
   a user control activatable by a first person to initiate a request to activate the voice recorder to record a spoken message;
   a processor operably coupled to the voice recorder and the user control;
   communication circuitry operably coupled to the processor and configured to connect the point of care device to a patient-nurse communication system; and
   a memory device having embodied therein at least one processor-executable routine configured to:
      determine whether the first person initiating the request to activate the voice recorder is authorized to activate the voice recorder based on an identity of the first person as determined from a first wireless signal emitted by a first tag worn by the first person;
      activate the voice recorder in response to determining that the person initiating the request is authorized to activate the voice recorder;
      record the spoken message;
      receive from the user control an input from the first person initiating the request indicating at least one second person who is authorized to listen to the recorded message;
      store the recorded message for future playback at the point of care device or at another device connected to the patient-nurse communication system, the recorded message being accessible only by the first person initiating the request and the at least one second person who is authorized to listen to the recorded message such that persons not authorized to record or access messages are unable to do so;
      transcribe the recorded message and store the transcribed message;
      validate the transcribed message prior to sending the transcribed message to a remote electronic medical record system; and
      send the transcribed message to the remote electronic medical record system.

7. The point of care communication device of claim 6, wherein the at least one processor-executable routine is configured to associate the recorded message with the identity of the person recording the spoken message.

8. The point of care communication device of claim 6, wherein the at least one processor-executable routine is configured to associate the recorded message with the at least one second person.

9. The point of care communication device of claim 8, wherein the at least one processor-executable routine is configured to play the recorded message in response to a request for playback received from the at least one second person.

10. The point of care communication device of claim 9, wherein the at least one processor-executable routine is configured to send the recorded message to another device associated with the at least one second person.

11. The point of care communication device of claim 6, wherein the at least one processor-executable routine is configured to determine a message type associated with the recorded message, the message type comprising at least one of: a message intended for playback by the first person, a message intended for playback by the at least one second person, a message intended to be associated with a person's electronic medical record, a message intended to be associated with the point of care communication device, a message intended to be associated with location at which the point of care communication device is located, a message intended to be associated with a device or piece of equipment at the location at which the point of care device is located; and determining whether to allow playback of the recorded message at the point of care communication device based on the message type.

12. The point of care communication device of claim 11, comprising a display configured to display a list of recorded messages available for playback at the point of care communication device, wherein the at least one processor-executable routine is configured to determine whether to include a recorded message in the list of recorded messages displayed at the point of care communication device based on at least one of the message type and information about a person requesting playback of a recorded message.

13. The user station of claim 1, wherein the input from the first person indicating the at least one second person is selected from a list having at least two of the following which are displayed on the user interface: one or more particular caregivers, housekeeping personnel, service technicians, and a patient's family members.

14. The user station of claim 1, wherein the input from the first person indicating the at least one second person is selected from a list having at least three of the following which are displayed on the user interface: one or more particular caregivers, housekeeping personnel, service technicians, and a patient's family members.

15. The point of care communication device of claim 6, wherein the input from the first person indicating the at least one second person is selected from a list having at least two of the following: one or more particular caregivers, housekeeping personnel, service technicians, and a patient's family members.

16. The point of care communication device of claim 6, further comprising a display screen that is operable to display a list of pending real-time calls placed by patients and that is operable to display a list of recorded voice messages.

* * * * *